United States Patent [19]

Bertozzi

[11] 4,374,142

[45] Feb. 15, 1983

[54] BISDITHIOCARBAMATE ESTERS OF DI-LOWER ALKYL FORMALS

[75] Inventor: Eugene R. Bertozzi, Yardley, Pa.

[73] Assignee: Thiokol Corporation, Newtown, Pa.

[21] Appl. No.: 196,899

[22] Filed: Oct. 14, 1980

Related U.S. Application Data

[60] Division of Ser. No. 125,830, Feb. 29, 1980, abandoned, which is a continuation of Ser. No. 766,660, Feb. 8, 1977, abandoned.

[51] Int. Cl.$^3$ .................... A01N 43/40; A01N 43/48; A01N 43/78; A01N 47/10
[52] U.S. Cl. .................................... 424/270; 424/246; 424/248.5; 424/250; 424/263; 424/267; 424/274; 424/286; 548/157
[58] Field of Search .......................... 424/270; 548/157

[56] References Cited

U.S. PATENT DOCUMENTS

| | | | |
|---|---|---|---|
| 1,835,050 | 12/1931 | Howland | 260/793 |
| 1,869,862 | 8/1932 | Orthner | 260/793 |
| 1,873,934 | 8/1932 | Lommel et al. | 525/352 |
| 2,285,077 | 6/1942 | Beaver | 260/786 |
| 2,424,175 | 7/1947 | Jones et al. | 260/785 |
| 2,619,481 | 11/1952 | Baldwin et al. | 525/333 |
| 3,705,923 | 12/1972 | Sullivan | 260/608 |
| 3,725,363 | 4/1973 | Albert | 525/348 |
| 3,869,435 | 3/1975 | Trivette, Jr. | 525/348 |

FOREIGN PATENT DOCUMENTS 1172771 10/1958 France.

*Primary Examiner*—Allen J. Robinson
*Attorney, Agent, or Firm*—James C. Lydon; Royal E. Bright

[57] ABSTRACT

Bisdithiocarbamate esters of di-lower alkyl formals and related compounds are disclosed. The final products are useful as rubber cure accelerators, biocides, antioxidants, corrosion inhibitors, and sulfur bearing oil additives.

6 Claims, No Drawings

BISDITHIOCARBAMATE ESTERS OF DI-LOWER ALKYL FORMALS

This application is a division of application Ser. No. 125,830, filed Feb. 29, 1980, now abandoned, which is in turn a continuation of application Ser. No. 766,660 filed 2/8/77, now abandoned.

BACKGROUND OF THE INVENTION

This invention relates to bisdithiocarbamate esters of di-lower alkyl formals, polymers thereof, and compounds structurally analogous thereto and processes for their preparation and use.

SUMMARY OF THE INVENTION

The invention provides a compound of the Formula I

wherein Q is

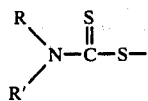

wherein R and R' are independently hydrogen, alkyl of from 1 to 10 carbon atoms, alkenyl of from 3 to 10 carbon atoms, alkynyl of from 3 to 10 carbon atoms, carbocyclic aryl of 6 or 10 carbon atoms in the aryl nucleus, heterocyclic aryl of 1 or 2 hetero atoms and 3 to 9 carbon atoms in the aryl nucleus, aralkyl wherein the aryl portion is heterocyclic or carbocyclic aryl as hereinbefore defined, and the alkyl is as hereinbefore defined, the hydrocarbyl portions of the aforedescribed moieties being either further unsubstituted or substituted with alkyl, alkenyl, alkynyl, as hereinbefore defined, hydroxy or alkoxy of 1 to 10 carbon atoms in the alkyl residue; or R and R' are concatenated and when taken together with the nitrogen atom form piperidino, pyrrolidino, morpholino, piperazino, pyridino, pyridazino, tetrahydro-thiazolo, dehydroindolo, tetrahydro-oxazolo, or thiamorpholino; or (B) 2 mercaptothiazolo either unsubstituted or substituted with alkyl, or aryl as hereinbefore defined, or fused to mono or bicyclic heteroaryl or carbocyclic aryl nucleus as hereinbefore defined; or

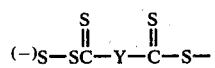

wherein Y is alkylene diamine, of from 2 to about 10 carbon atoms, cyclo alkylene diamine having 5 or 6 carbon atoms in the cyclo alkylene ring, alkenylene diamine of 4 to 10 carbon atoms, cyclo alkenylene diamine having 5 or 6 carbon atoms in the cyclo alkenylene ring, alkynylene diamine of from 4 to 10 carbon atoms, or

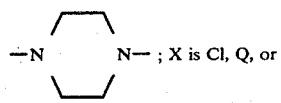

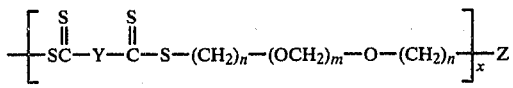

wherein Y is as hereinbefore defined, Z is Q or Cl, and x is sufficient to give a total molecular weight of 1000; n is an integer of from 2 to about 10; m is O or an integer of from 1 to 3, with the proviso that if m is O then X is

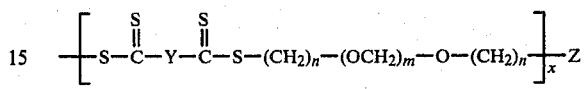

wherein Y, n, m and Z are as defined hereinabove; and the addition salts thereof.

The tangible embodiments of this composition aspect of the invention possess the inherent applied use characteristics of being antioxidants, corrosion inhibitors, sulfur bearing oil additives, biocides for inhibiting the growth of plant infections and when X is identical to Q and Q and X are as defined for Formula I under (A) or (B), as rubber cure accelerators.

Preferred embodiments of the compounds of Formula I are those wherein m is 1.

The invention also provides a curable composition comprising
 (a) a vulcanizable rubber; and
 (b) a compound of Formula I wherein Q is (A) or (B) and X is identical to Q, and m and n are as defined for Formula I.

The tangible embodiments of this composition aspect of the invention possess the inherent applied use characteristics of being curable to cured rubber at a greater rate when treated with conventional rubber curing agents than the corresponding vulcanizable rubbers alone.

The invention also provides a method for the control of plant diseases which comprises the application, to a plant or to the soil immediately surrounding said plant, of a compound of Formula I.

DESCRIPTION OF THE PREFERRED EMBODIMENT

The manner of making and using the compositions of the invention will now be described with reference to a specific embodiment thereof namely Bis-(dimethyl dithiocarbamyl ethyl) formal (II).

To prepare II, dimethyl amine may be treated with approximately stoichiometric amounts of carbon disulfide and aqueous sodium hydroxide while removing heat from the exothermic reaction which ensues. When the reaction mixture containing the dimethyl dithiocarbamic acid sodium salt has become homogeneous an approximately one half equivalent of Bis-(2-chloroethyl) formal may be added slowly while warming, conveniently at a temperature between 60° C. and the reflux temperature of the solution, preferably at about 80° C., the reaction mixture is maintained in this temperature range with occasional addition of small portions of deionized water and subsequent removal of the aqueous phase from the two phase system until the pH of the reaction mixture remains at about 7. II may, if desired, be recovered by standard techniques, conveniently by dilution of the cooled reaction mixture with additional deionized water followed by recovery of the resulting precipitated product by filtration and drying.

It will be obvious to one skilled in the art that substitution of other known amines for the dimethyl amine illustrated and of other known bis-(ω-halo alkyl)- ethers and formals for the bis-(2-chloro ethyl) formal illustrated in analogous procedures will permit the preparation of the other compounds of Formula I wherein m is 0 or 1. Compounds of formula $$Cl\text{-}(CH_2)_n\text{-}(O\text{-}CH_2)_m\text{-}O\text{-}(CH_2)_n\text{-}Cl$$

wherein n is as defined hereinabove and m is 2 or 3 may be prepared by condensing α-ω halo alkyl compounds with formaldehyde in the presence of an acid catalyst as for the preparation of the analogous compounds wherein m is 1 but doubling or tripling the proportion of formaldehyde for m=2 and m=3 respectively, and controlling the temperature to the minimum needed for water removal. These compounds may also be substituted for the bis-(2-chloro ethyl) formal illustrated to prepare the compounds of Formula I wherein m=2 or 3 as desired.

It will also be recognized that with mono amines monomeric products will be produced and that control of the relative molar proportions of dithio carbonate salt and dihalo formal or ether reactant will permit substitution for 1 or both halogens. Similarly it will be apparent that if diamines are used the proportions of carbon disulfide and sodium hydroxide may be varied to permit reaction with one or both amino functions. Naturally if only the dithiocarbamate is formed then reaction with the dihalo formals or ethers will proceed as in the case of mono amines. On the other hand, if two dithiocarbamate functions are created then reaction with equal molar proportions of the dihalo compounds will result in polymers ranging up to a molecular weight of about 1000. It is assumed that in this case one end of the polymer will have a halo terminal and the other end a dithiocarbamate terminal although one skilled in the art will recognize that molecules containing terminals solely of either functional group may also form.

If, however, a substantial excess of the bis-dithiocarbamate compound or the dihalo compound relative to the other reactant is employed then polymer formation will be inhibited and low molecular weight adducts will be formed, for example, for a 2 to 1 molar ratio of reactants a compound of the type D-E-D where D is the residue of the reactant with the higher mole ratio and E is the residue of the reactant with the lower mole ratio, will be formed.

The mercapto thiazole derivatives contemplated as part of Formula I may be prepared from the sodium salts of known mercapto thiazoles and the aforementioned dihalo compounds in a fashion analogous to that employed for the other compounds of Formula I. Preparation of mercapto thiazoles from aromatic amines and carbon disulfide or from 2 hydroxy mono aliphatic mono amines and carbon disulfide are well known to the art.

In using the compositions of the invention, particularly the compounds of Formula I when X is identical to Q and Q and X are as defined in (A) or (B) thereunder, as rubber cure accelerators their use in combination with or instead of other known rubber cure accelerators in conventional known rubber formulations is contemplated. The formulations will be of those natural and synthetic rubbers known to undergo sulfur cure but will not necessarily be sulfur cure formulations. Other conventional rubber curing agents known in the art to replace sulfur as curing agents for rubber may be employed.

When using the compositions of the invention as biocides for the treatment or prevention of plant diseases their application may be to the seed, the whole, or the affected part of the plant or to the soil immediately surrounding the plant, as has been found to be effective in the art for appropriate treatment of the particular pathogen in question. Application may, of course, be of the compound by itself or in combination with an agriculturally acceptable carrier in the form of powder, or liquid either by spray, dusting, washing, or, if convenient, immersion of the treatment subject. The dosage will quite naturally vary with the severity of the infestation, nature of the pathogen, nature of the subject plant being treated and the mode of application. Generally as the compounds are, with the possible exception of certain mercaptothiazole derivatives, relatively non-toxic to plants, dosages in excess of the minimum required for effect against the pathogen will not be expected to be deleterious on non food crops. Normally, application of a graded series of concentrations will allow selection of concentrations effective against a pathogen and which will not exhibit permanent toxic effects on a particular plant species. On food crops, of course, application should be such that resides of the compounds will be minimal at the time of harvest on at least the edible portions. Generally an aqueous suspension containing between 1 and 10,000 ppm of active ingredient preferably between 100 and 1000 ppm, applied as a spray may be employed.

When using the compositions of the invention as antioxidants, corrosion inhibitors or sulfur bearing oil additives they may be used in combination with or in place of other known antioxidants, corrosion inhibitors and sulfur bearing oil additives in similar formulations to those now employed for these purposes.

As used herein and in the appended claims the term alkyl means straight, branched chain or cyclic alkyl radicals, such as, but without limitation thereto, methyl, ethyl, i-butyl, cyclohexyl and the like. The term alkenyl means a straight, branched chain or cyclic alkenyl radical with the limitation that when it is attached to a nitrogen atom no non-aromatic unsaturation may be present in the 1,2 position such as, but without limitation thereto, 2-propenyl, 2-butenyl, 2-cyclohexenyl, 3-methyl-2-pentenyl, and the like. The term alkynyl means straight or branched chain alkynyl radicals with the proviso that no non-aromatic unsaturation is in the 1,2 position, such as, but without limitation thereto, 2-propynyl, 2-butynyl, 4 methyl-2-pentynyl and the like.

The term addition salts contemplates cationic salts of thiocarbamate functions of a particular molecule which may be available for salt formation. The cationic salts contemplated include those of the alkali and alkali earth metals such as sodium, potassium, calcium, magnesium or the like, heavy metals such as iron and copper and cations derived from ammonia or a basic amine. The term cation derived from ammonia or a basic amine contemplates the positively charged ammonium ion and analogous ions derived from organic nitrogenous bases strong enough to form such cations. Bases useful for this purpose form a class whose limits are well understood by those skilled in the art. Merely for illustration, they can be said to comprise in cationic form those of the formula

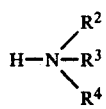

wherein $R^2$, $R^3$ and $R^4$ are independently, are hydrogen, alkyl of from 1 to about 10 carbon atoms, mono carbocyclic aryl of about 6 carbon atoms, mono carbocyclic aryl alkyl of from about 7 to about 11 carbon atoms, hydroxy alkyl of from about 1 to about 3 carbon atoms or mono carbocyclic aryl hydroxy alkyl of from about 7 to about 15 carbon atoms, or when taken together with the nitrogen atom to which they are attached any two of $R^2$, $R^3$ and $R^4$ form part of a 5 or 6 membered heterocyclic rings and said mono carbocyclic aryl groups being unsubstituted or mono or dialkyl substituted, said alkyl groups containing from 1 to about 10 carbon atoms.

Illustrative of cations derived from ammonia or a basic amine are ammonium, mono-, di-, and trimethyl ammonium, mono-, di-, and triethyl ammonium, mono-, di-, and tripropyl-ammonium (iso and normal), ethyl dimethyl ammonium, benzyl dimethyl ammonium, cyclo hexyl ammonium, benzyl ammonium, dibenzyl ammonium, piperidinium, morpholinium, pyrrolidinium, piperazinium, 1-methyl piperidinium, 4-ethyl morpholinium, 1-isopropyl pyrrolidinium, 1,4-dimethyl piperazinium, 1-n-butyl piperidinium, 2-methyl piperidinium, 1-ethyl-2-methyl piperidinium, mono-, di-, and triethanol ammonium, ethyl diethanol ammonium, n-butyl-mono-ethanol ammonium, tris(hydroxy methyl) methyl ammonium, phenyl mono-ethanol ammonium, and the like. Also contemplated are acid addition salts of those compounds of Formula I which have a nitrogen function capable of forming such acid addition salts. The salts contemplated are those of both organic and inorganic acids such as hydrochloric, hydrobromic, sulfuric, nitric, phosphoric, methane sulfonic, benzene sulfonic, and the like.

One skilled in the art will, or course, recognize that free dithiocarbamic acids are unstable and that consequently conversion from one cationic salt form to another is most conveniently accomplished by passing a solution of one salt form through a cationic ion exchanger charged with the cation the salt of which is desired. The acid addition salts may be conveniently prepared by mixing aqueous solutions of the acids and the appropriate nitrogen base compound and drying. Obviously no thiocarbamate salt functions may be present in a compound which is to be converted to an acid addition salt.

The term agriculturally acceptable carrier contemplates usual and customary substances including, but not limited to water, kerosene, alcohol, and dimethyl sulfoxide employed for formulating suspensions, solutions or powder dosage forms for application to seeds, plants or soil for treatment of pathogen infestations, it also includes those forms prepared either dry or as a concentrate for later reconstitution to dosage form for application.

The following Examples further illustrate the best mode contemplated by the inventor for the practice of his invention.

EXAMPLE 1

Bis(2-dimethyl dithiocarbamyl-ethyl) formal

A. To a 25% aqueous solution of dimethyl amine (1.0 mole) is added solid sodium hydroxide (1.0 mole) while stirring and cooling. When the mixture has cooled to 30° C. carbon disulfide (1.0 mole) is added slowly enough to maintain the temperature of the mixture at about 30° C. while stirring. After stirring at about 30° C. for about 4.5 hours the mixture becomes homogeneous.

B. To the aqueous solution of dimethyl dithiocarbamic acid prepared in A above is added bis (2-chloro ethyl) formal (0.5 mole) while heating at 60° C. After all the formal has been added the reaction is heated at reflux for about ½ hour then permitted to stand at ambient temperature for about 16 hours. Two phases are present with the aqueous phase giving an alkaline reaction in the range of pH 12. The reaction mixture is then warmed over a period of about 4 hours to about 70° to about 80° C. while stirring. After about 1 hour a small quantity of deionized water is added and after thorough mixing the aqueous layer is decanted. More deionized water is then added and again decanted after thorough mixing. This procedure is followed twice more during a 2 hour period with the pH of the aqueous layer remains at a constant 7. Following the final decantation cold deionized water is added slowly while stirring the warm reaction mixture. A granular precipitate is obtained. Upon filtration and drying of the precipitate to constant weight the title product is obtained (84.9%) M. Pt. Softens 68°-75° C., Melts 78°-82° C.

EXAMPLE 2

Bis[-2-(2-mercapto benzothiazolyl)ethyl]formal

To mercaptobenzothiazole (1 mole) is added sodium hydroxide (1 mole as 25% solution) followed by stirring of the mixture for 1 hour. The mixture is then warmed to about 60° to 70° C. and stirred for an additional hour. Bis-(2-chloro-ethyl) formal (½ mole) is then added slowly with stirring while maintaining the temperature between 60° C. and 70° C. After all the formal is added the reaction mixture is refluxed for 2 hours. Heating is then stopped and about 500 ml H₂O added. An oil layer separates which is partitioned and washed with water until the pH of the washings is about 6. The oily product is then dried by dilution with toluene followed by vacuum distillation of the solvent in vacuo. 89.4% is the yield of title product so obtained.

EXAMPLE 3

Bis-(2-N-morpholinothiocarbonylmercaptoethyl)-formal

To sodium hydroxide (1 mole) dissolved in 120 g H₂O is added morpholine (1 mole) while stirring and maintaining the temperature at about 30° C. After all the morpholine is added, carbon disulfide (1 mole) is added at a rate sufficient to maintain the temperature of the mixture at about 35° C. After all carbon disulfide is added additional water (120 ml) is added to bring all solid material into solution, and the mixture is held at 30° C. for 1 hour. The mixture is then warmed to 60° C. and bis-(2-chloroethyl) formal (½ mole) is added over a period of about 1 hour. After all the formal is added, the reaction mixture is then warmed to between 90° and 100° C. for 1 hour. By the end of this period the reaction mixture separates into 2 phases.

After cooling the aqueous phase was decanted and the residual oil washed with successive portions of hot water until the washings were negative to silver nitrate for chloride ion and were at pH 7. Addition of ice to the residual product causes solidification. Removal of water and vacuum drying over drierite gives the title product (86.9%).

EXAMPLE 4

Bis-(Di-isopropanolyldithiocarbamyl ethyl)-formal

To sodium hydroxide (1 mole) dissolved in water (120 ml) are added diisopropanolamine (1 mole) and carbon disulfide (1 mole) while stirring. Following addition of the carbon disulfide the mixture is warmed to about 60° C. and bis-(2-chloroethyl) formal (½ mole) is then added. Following addition of the formal the reaction mixture is heated to reflux while continuing to stir. After about 3½ hours the reaction is cooled and then the oily product which separates is partitioned, washed with successive portions of fresh water to pH 7 and negative silver nitrate chloride test. Following dilution with and removal of toluene in vacuo and drying to constant weight, the title product is obtained (75.5%).

EXAMPLE 5

Bis-(2-di-2-hydroxy ethyl dithiocarbamyl ethyl) formal

Following a procedure analogous to that of Example 4, there is obtained from diethanol amine (1 mole) sodium hydroxide (1 mole), carbon disulfide (1 mole) and bis-(2-chloroethyl) formal (½ mole) 62.3% of the title product.

EXAMPLE 6

Poly-bis-[2-(4-dithiocarboxyl piperazino thiocarbamyl mercapto)ethyl] formal

To 6.0 moles of sodium hydroxide dissolved in H$_2$O (720 ml) is added piperazine (3.0 moles) over a ½ hour period. To this mixture while stirring and cooling below 35° C. is added, over a period of 1 hour, carbon disulfide (6.0 moles). Cooling is required for an additional hour after all the carbon disulfide is added. The reaction mixture is warmed to 90° C. and bis-(2-chloroethyl) formal (3.0 moles) is added at a rate sufficient to maintain the temperature in the vicinity of 90° C. After all the formal is added, the reaction mixture is stirred at 90° C. for an additional 3 hours. The white insoluble product which forms is removed from the reaction, cooled, pulverized and washed free of chloride ion with water. The title product so obtained as the sodium salt is dried to constant weight at 60° C. and 1.0 mm vacuum (96% yield).

EXAMPLE 7

Poly-bis-(2-dithiocarbamyl ethylene dithiocarbamyl ethyl) formal

To sodium hydroxide (6.0 moles) dissolved in H$_2$O (480 ml) is added ethylene diamine slowly while stirring and with sufficient external cooling to maintain the temperature at or below 30° C. Carbon disulfide (6.0 moles) is then added slowly while stirring and cooling to below the reflux temperature. After the carbon disulfide addition is complete reflux is allowed to continue until the reaction moderates. The reaction mixture is then warmed to 85° C. and bis-(2-chloroethyl) formal (3.0 moles) is added over a 1 hour period. After formal addition was complete the solution was kept at 85° C. for an additional 2 hours. A product separates which is partitioned from the aqueous layer, washed with hot water to pH 6 and a negative silver nitrate chloride test and dried at 75° C. and 1 to 2 mm vacuum to give the title product as a sodium salt (94.9% yield).

EXAMPLE 8

Bis[2-(2-mercapto thiazoyl) ethyl] formal

To sodium hydroxide (1 mole) in water (120 g) is added while stirring and maintaining the temperature below 30° C. monoethanolamine (1 mole). When addition is complete carbon disulfide (1 mole) is added while maintaining the temperature at about 35° C. The reaction mixture is then warmed to 90° C. and after holding at this temperature for about ½ hour Bis-(2-chloroethyl) formal (0.5 mole) is added. The soluion is then heated at reflux for about 3 hours. The oil which separates on cooling is washed to pH 7 and negative silver nitrate chloride test, and vacuum dried.

EXAMPLE 9

The compounds of Examples 1, 2, 3, 4, 6 and 8 are prepared as aqueous suspensions by dissolving known quanities of the compounds in acetone (10 ml) adding a drop of Tween 20 (sorbitan monolaurate polyoxyalkylene derivative supplied by Atlas Powder Co.) and diluting to serial concentrations with water. These suspensions were then used for treatment of infected plants as indicated below by spraying the suspension on the leaf surfaces to run, or in the case of root-knot nematode by applying the suspension to the soil prior to infestation of the soil with nematode larvae.

Tests were conducted against bacterial, fungal, viral, and nematode diseases. Concurrent comparison was run against (a) foliage and root pathogens, (b) superficial and internal pathogens, and (c) facultative and obligate parasites. Fungi, the most common cause of plant disease, are composed of 3 classes, phycomycetes, ascomycetes, and basidomycetes. Representatives of each class were included in the assay. The diseases examined are all of economic importance.

Tomato plants were in the 5–6 leaf stage, bean seedlings had their primary leaves two-thirds expanded and the second leaf was just emerging in wheat at the time of treatment. One or two days after treatment the plants or soil as appropriate were innoculated with the appropriate pathogen. The results obtained are shown in the following Tables:

TABLE 1

| | Early (Alternaria) blight of tomato | | | |
|---|---|---|---|---|
| Compound of Example No. | Conc. ppm | No. lesions/ leaf[a] | % Disease reduction | Comments |
| Untreated | — | 209 | — | No injury |
| 1 | 1000 | 67 | 68 | No injury |
|   | 100 | 107 | 49 | |
| 2 | 1000 | 22 | 90 | Interveinal chlorosis |
|   | 100 | 95 | 55 | of newly emerging leaves |
| 3 | 1000 | 72 | 66 | No injury |
|   | 100 | 156 | 25 | |
| 4 | 1000 | 128 | 39 | No injury |
|   | 100 | 173 | 17 | |
| 6 | 1000 | 231 | 0 | No injury |
|   | 100 | 206 | 2 | |
| 8 | 1000 | 141 | 32 | No injury |
|   | 100 | 225 | 0 | |
| Maneb[b] | 100 | 105 | 50 | No injury |

TABLE 1-continued

Early (Alternaria) blight of tomato

| Compound of Example No. | Conc. ppm | No. lesions/leaf[a] | % Disease reduction | Comments |
|---|---|---|---|---|
| | 10 | 142 | 32 | |
| | 1 | 218 | 0 | |

[a]Lesions counted on 3rd leaf from cotyledons.
[b]Maneb is [ethylene bis(dithiocarbamato)] manganese.

TABLE 2

Wheat leaf rust

| Compound of Example No. | Conc. ppm | No. pustules/basal leaf | % Disease reduction | Comments |
|---|---|---|---|---|
| Untreated | — | 36 | — | No injury |
| 1 | 1000 | 4 | 89 | No injury |
| | 100 | 14 | 61 | |
| 2 | 1000 | 3 | 92 | No injury |
| | 100 | 12 | 67 | |
| 3 | 1000 | 9 | 75 | No injury |
| | 100 | 32 | 11 | |
| 4 | 1000 | 9 | 75 | No injury |
| | 100 | 29 | 20 | |
| 6 | 1000 | 18 | 50 | No injury |
| | 100 | 27 | 25 | |
| 8 | 1000 | 4 | 89 | No injury |
| | 100 | 25 | 31 | |
| Maneb | 100 | 2 | 95 | No injury |
| | 10 | 9 | 75 | |
| | 1 | 19 | 47 | |

TABLE 3

Late (Phytophthora) Blight of Tomato

| Compound of Example No. | Conc. ppm | % of leaf necrotic[a] | % Disease reduction | Comments |
|---|---|---|---|---|
| Untreated | — | 80 | — | No injury |
| 1 | 1000 | 80 | 0 | No injury |
| | 100 | 77 | 4 | |
| 2 | 1000 | 83 | 0 | Interveinal chlorosis of newly emerging leaves |
| | 100 | 83 | 0 | |
| 3 | 1000 | 30 | 62 | No injury |
| | 100 | 63 | 21 | |
| 4 | 1000 | 50 | 37 | No injury |
| | 100 | 70 | 12 | |
| 6 | 1000 | 67 | 16 | No injury |
| | 100 | 67 | 16 | |
| 8 | 1000 | 57 | 29 | No injury |
| | 100 | 83 | 0 | |
| Maneb | 100 | 7 | 91 | No injury |
| | 10 | 16 | 80 | |
| | 1 | 53 | 44 | |

[a]Disease estimated on 3rd leaf from cotyledon.

TABLE 4

Bean powdery mildew

| Compound of Example No. | Conc. ppm | No. lesions/primary leaf | % Disease reduction | Comments |
|---|---|---|---|---|
| Untreated | — | 147 | — | No injury |
| 1 | 1000 | 156 | 0 | No injury |
| | 100 | 156 | 0 | |
| 2 | 1000 | 8 | 95 | Many incipient lesions |
| | 100 | 122 | 17 | Interveinal chlorosis of newly emerging leaves |
| 3 | 1000 | 162 | 0 | No injury |
| | 100 | 151 | 0 | |
| 4 | 1000 | 156 | 0 | No injury |
| | 100 | 161 | 0 | |

TABLE 4-continued

Bean powdery mildew

| Compound of Example No. | Conc. ppm | No. lesions/primary leaf | % Disease reduction | Comments |
|---|---|---|---|---|
| 6 | 1000 | 154 | 0 | No injury |
| | 100 | 135 | 8 | |
| 8 | 1000 | 148 | 0 | No injury |
| | 100 | 148 | 0 | |
| Benomyl[a] | 5 | 149 | 0 | No injury |

[a]Benomyl is methyl 1-(butyl carbamoyl)-2-benzimidazol carbamate.

TABLE 5

Fusarium wilt of Tomato

| Compound of Example No. | Conc. ppm | Disease indices[a] | % Disease reduction | Comments |
|---|---|---|---|---|
| Untreated | — | .87 | | No injury |
| 1 | 1000 | .87 | 0 | No injury |
| | 100 | .68 | 22 | |
| 2 | 1000 | 1.0 | 0 | Interveinal chlorosis on newly emerging leaves |
| | 100 | .78 | 10 | |
| 3 | 1000 | .65 | 25 | No injury |
| | 100 | .91 | 0 | |
| 4-DIPA | 1000 | .63 | 27 | No injury |
| | 100 | .74 | 15 | |
| 6 | 1000 | .74 | 15 | No injury |
| | 100 | .87 | 0 | |
| 8 | 1000 | .82 | 6 | No injury |
| | 100 | .87 | 0 | |

[a]Ratio of the number of internodes with discolored vessels to the total number of internodes.

TABLE 6

Bacterial wilt of tomato

| Compound of Example No. | Conc. ppm | Disease indices[a] | % Disease reduction | Comments |
|---|---|---|---|---|
| Untreated | — | .95 | — | |
| 1 | 1000 | .95 | 0 | |
| | 100 | 1.0 | 0 | |
| 2 | 1000 | 1.0 | 0 | Interveinal chlorosis of newly emerging leaves |
| | 100 | .95 | 0 | |
| 3 | 1000 | .85 | 10 | |
| | 100 | .91 | 4 | |
| 4 | 1000 | .95 | 0 | |
| | 100 | .81 | 15 | |
| 6 | 1000 | .90 | 5 | |
| | 100 | .95 | 0 | |
| 8 | 1000 | .91 | 4 | |
| | 100 | .95 | 0 | |

[a]Ratio of number of leaves wilted to the total number of leaves.

TABLE 7

Bacterial spot of tomato

| Compound of Example No. | Conc. ppm | No. lesions/leaf[a] | % Disease reduction | Comments |
|---|---|---|---|---|
| Untreated | — | 165 | — | No injury |
| 1 | 1000 | 46 | 72 | No injury |
| | 100 | 39 | 76 | |
| 2 | 1000 | 0 | 100 | Many undeveloped lesions |
| | 100 | 120 | 27 | Leaf chlorosis and necrosis |
| 3 | 1000 | 27 | 84 | No injury |
| | 100 | 44 | 73 | |
| 4 | 1000 | 54 | 67 | No injury |

TABLE 7-continued

Bacterial spot of tomato

| Compound of Example No. | Conc. ppm | No. lesions/leaf[a] | % Disease reduction | Comments |
|---|---|---|---|---|
|  | 100 | 129 | 22 |  |
| 6 | 1000 | 73 | 56 | No injury |
|  | 100 | 146 | 12 |  |
| 8 | 1000 | 51 | 69 | No injury |
|  | 100 | 94 | 43 |  |
| Streptomycin | 100 | 33 | 80 | No injury |

[a]Lesions counted on 3rd leaf from cotyledon.

TABLE 8

Southern bean mosaic virus on bean seedlings

| Compound of Example No. | Conc. ppm | No. lesions/primary leaf | % Disease reduction | Comments[a] |
|---|---|---|---|---|
| Untreated | — | 236 |  | Slight leaf burn |
| 1 | 1000 | 233 | 1 | Slight leaf burn |
|  | 100 | 239 | 0 |  |
| 2 | 1000 | 241 | 0 | Interveinal chlorosis of newly emerging leaves |
|  | 100 | 215 | 8 |  |
| 3 | 1000 | 236 | 0 | Mod.-sev. leaf burn |
|  | 100 | 224 | 5 |  |
| 4 | 1000 | 205 | 13 | Severe leaf burn |
|  | 100 | 222 | 6 |  |
| 6 | 1000 | 237 | 0 | Moderate leaf burn |
|  | 100 | 198 | 16 |  |
| 8 | 1000 | 228 | 3 | Slight leaf burn |
|  | 100 | 207 | 12 |  |
| Thiouracil | 1000 | 1 | 99 | Moderate leaf burn |

[a]Leaf injury in untreated bean plants is due to carborundum injury incurred during inoculation. Leaf injury exacerbated in treated leaves.

TABLE 9

Root-knot nematode in tomato

| Compound of Example No. | Conc. mg/50 ml | No. of root galls/plant | % Disease reduction | Comments |
|---|---|---|---|---|
| Untreated | — | 344 | — | No injury |
| 1 | 50 | 299 | 13 | No injury |
|  | 5 | 305 | 11 |  |
| 2 | 50 | 335 | 3 | No injury |
|  | 5 | 366 | 0 |  |
| 3 | 50 | 390 | 0 | No injury |
|  | 5 | 335 | 3 |  |
| 4 | 50 | 335 | 3 | No injury |
|  | 5 | 325 | 6 |  |
| 6 | 50 | 328 | 5 | No injury |
|  | 5 | 333 | 3 |  |
| 8 | 50 | 331 | 4 | No injury |
|  | 5 | 360 | 0 |  |

TABLE 10

Summary of Tables 1-8

Per cent disease reduction

| Compound of Example No. | Conc. ppm | Early blight | Leaf rust | Late blight | Powdery Mildew | Bacterial Spot |
|---|---|---|---|---|---|---|
| Untreated | — |  |  |  |  |  |
| 1 | 1000 | 68 | 89 | 0 | 0 | 72 |
|  | 100 | 49 | 61 | 4 | 0 | 76 |
| 2 | 1000 | 90 | 92 | 0 | 95 | 100 |
|  | 100 | 55 | 67 | 0 | 17 | 27 |
| 3 | 1000 | 66 | 75 | 62 | 0 | 84 |
|  | 100 | 25 | 11 | 21 | 0 | 73 |
| 4 | 1000 | 39 | 75 | 37 | 0 | 67 |
|  | 100 | 17 | 20 | 12 | 0 | 22 |
| 6 | 1000 | 0 | 50 | 16 | 0 | 56 |
|  | 100 | 2 | 25 | 16 | 8 | 12 |
| 8 | 1000 | 32 | 89 | 29 | 0 | 69 |
|  | 100 | 0 | 31 | 0 | 0 | 43 |
| Maneb | 100 | 50 | 95 | 91 | — | — |
|  | 10 | 32 | 75 | 80 | — | — |
|  | 1 | 0 | 47 | 44 | — | — |
| Benomyl | 5 | — | — | — | 0 | — |
| Streptomycin | 100 | — | — | — | — | 80 |

EXAMPLE 10

Rubber formulations are prepared and cured using known cure accelerators and the compounds of the invention in parallel formulations. The formulations and the physical properties of the cured materials are as shown.

FORMULATION A

| Material | Quantity Parts by Weight | |
|---|---|---|
| Nordel 1070 (Ethylene propylene terpolymer, duPont) | 100 | 100 |
| SAF Black (Carbon Black) | 130 | 130 |
| Circolite (Sun Oil Co.-hydrocarbon oil rubber extender) | 100 | 100 |
| Zinc Oxide | 5 | 5 |
| Stearic Acid | 1 | 1 |
| Tetramethyl thiuram disulfide | 1.5 | 1.5 |
| Mercaptobenzo Thiazole | 0.5 | — |
| Compound of Example 2 | — | 0.5 |
| Sulfur | 1.5 | 1.5 |
| Physical Properties after cure at 320° F. for 30 min. | | |
| Tensile (psi) | 1650 | 2010 |
| Elongation (%) | 940 | 690 |
| 100% Modulus | 100 | 130 |
| 200% Modulus | 150 | 275 |

FORMULATION B

| Material | Quantity Parts by Weight | |
|---|---|---|
| SBR (Styrene-butadiene rubber) | 100 | 100 |
| HAF Black (Carbon Black) | 40 | 40 |
| Zinc Oxide | 5 | 5 |
| Stearic Acid | 1 | 1 |
| Circolite | 1 | 1 |
| Flectol H (Monsanto Co. Condensation product of aniline and acetone) | 3 | 3 |
| Mercaptobenzo thiazole | 2 | 2 |
| Bismate (R. T. Vanderbilt Co. Inc. rubber accelerator) | 2 | 2 |
| Compound of Example 1 | — | 2 |
| Sulfur | 1 | 1 |
| Physical Properties after cure at 320° F. for 20 min. | | |
| Tensile | 1750 | 3040 |
| Elongation (%) | 210 | 430 |
| 100% Modulus | 630 | 360 |
| 200% Modulus | 1640 | 875 |
| Duro A | 63 | 72 |

| FORMULATION C | | | |
|---|---|---|---|
| Material | Quantity Parts by Weight | | |
| SBR (Styrene-butadiene rubber) | 100 | 100 | 100 |
| HAF Black (Carbon Black) | 40 | 40 | 40 |
| Zinc Oxide | 5 | 5 | 5 |
| Stearic Acid | 1 | 1 | 1 |
| Circolite (?) | 1 | 1 | 1 |
| Flectol H | 3 | 3 | 3 |
| Mercaptobenzo thiazole | 2 | 2 | 2 |
| Bismate | 2 | — | — |
| Compound of Example 1 | — | 0.3 | 1 |
| Compound of Example 3 | — | 0.5 | 1 |
| Sulfur | 1.75 | 1.75 | 1.75 |
| Physical Properties after cure at 320° F. for 20 min. | | | |
| Tensile (psi) | 1880 | 3370 | 3670 |
| Elongation (%) | 180 | 520 | 600 |
| 100% Modulus | 925 | 300 | 270 |
| 200% Modulus | 2160 | 760 | 600 |
| Duro A | 75 | 62 | 63 |

Attempts to prepare a formulation similar to that of B or C herein for the compound of Example 6 were not successful due to difficulty in dispersing the solid compound when preparing the formulation mix.

The subject matter which applicant regards as his invention is particularly pointed out and distinctly claimed as follows:

1. A composition comprising
   (i) a biocide, in an amount effective to inhibit the growth of plant infections, which must conform to the formula

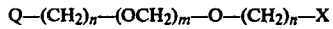

wherein Q is a 2-mercaptothiazole radical of the following formula

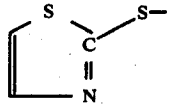

which is either unsubstituted or substituted with alkyl of from 1 to 10 carbon atoms, carbocyclic aryl of 6 or 10 carbon atoms in the aryl nucleus, or fused to a mono or bicyclic carbocyclic aryl of 6 or 10 carbon atoms in the aryl nucleus;
   X is a monovalent radical which is either Q or —Cl,
   n is an integer of from 2 to about 10;
   m is an integer of from 1 to 3
   (ii) an agriculturally acceptable carrier.

2. The biocide composition of claim 1 wherein the biocidally active compound is bis[2-(2-mercapto benzothiazolyl) ethyl] formal.

3. The biocidal composition of claim 1 wherein the biocidally active compound is bis[2-(2-mercapto thiazolyl) ethyl] formal.

4. A method for the control of plant diseases which comprises the application, to a plant or the soil immediately surrounding said plant, of an amount effective to inhibit the growth of plant infections of a composition comprising
   (i) a biocide, in an amount of effective to inhibit the growth of plant infections, which must conform to the formula

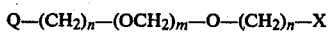

wherein Q is a 2-mercaptothiazole radical of the following formula

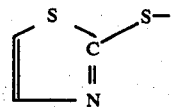

which is either unsubstituted or substituted with alkyl of from 1 to 10 carbon atoms, carbocyclic aryl of 6 or 10 carbon atoms in the aryl nucleus, or fused to a mono or bicyclic carbocyclic aryl of 6 or 10 carbon atoms in the aryl nucleus;
   X is a monovalent radical which is either Q, or —Cl,
   n is an integer from 2 to about 10
   m is an integer of from 1 to 3
   (ii) an agriculturally acceptable carrier.

5. The method of claim 4 wherein the biocide is bis [2-(2-mercapto benzothiazolyl)ethyl] formal.

6. The method of claim 4 wherein the biocide is bis[2-(2-mercapto thiazolyl) ethyl] formal.

* * * * *